United States Patent
Ikadai et al.

(10) Patent No.: US 7,399,297 B2
(45) Date of Patent: *Jul. 15, 2008

(54) SKIN CARE DEVICE FOR TAKING OUT AND REMOVING SEBUM OR OTHER CUTANEOUS IMPURITIES

(75) Inventors: Kazuyasu Ikadai, Osaka (JP); Mitsuru Fujiwara, Osaka (JP)

(73) Assignee: Matsushita Electric Works, Ltd., Osaka (JP)

( * ) Notice: Subject to any disclaimer, the term of this patent is extended or adjusted under 35 U.S.C. 154(b) by 48 days.

This patent is subject to a terminal disclaimer.

(21) Appl. No.: 11/037,075

(22) Filed: Jan. 19, 2005

(65) Prior Publication Data

US 2005/0159760 A1    Jul. 21, 2005

(30) Foreign Application Priority Data

Jan. 19, 2004    (JP)    .............................. 2004-011097

(51) Int. Cl.
```
A61M 1/00       (2006.01)
A61M 35/00      (2006.01)
A61H 7/00       (2006.01)
A61H 9/00       (2006.01)
A61B 17/50      (2006.01)
```
(52) U.S. Cl. ........................ 604/540; 604/310; 604/313; 604/315; 601/6; 601/159; 601/161; 606/131

(58) Field of Classification Search ......... 604/289–316, 604/540; 606/131; 601/6, 7, 10, 12, 154, 601/159–161; 132/218, 317, 320
See application file for complete search history.

(56) References Cited

U.S. PATENT DOCUMENTS

| | | | | |
|---|---|---|---|---|
| 2,710,114 | A | * | 6/1955 | Waber et al. ................. 221/232 |
| 6,309,364 | B1 | * | 10/2001 | Cathaud et al. ................. 601/7 |
| 6,319,211 | B1 | * | 11/2001 | Ito et al. ......................... 601/7 |
| 6,468,235 | B2 | * | 10/2002 | Ito et al. ......................... 601/6 |
| 2005/0159684 | A1 | * | 7/2005 | Ikadai ............................. 601/6 |
| 2005/0159761 | A1 | * | 7/2005 | Ikadai ......................... 606/131 |

FOREIGN PATENT DOCUMENTS

| | | |
|---|---|---|
| EP | 0997156 | 5/2000 |
| JP | S35-1984 | 3/1960 |
| JP | S51-118369 | 9/1976 |
| JP | 53-004648 A * | 1/1978 |

(Continued)

OTHER PUBLICATIONS

Machine generated English language translation of JP 2001-161438 A, generated at http://www.ipdl.inpit.go.jp/homepg_e.ipdl on May 1, 2007.*

*Primary Examiner*—T. Zalukaeva
*Assistant Examiner*—Michael G Bogart
(74) *Attorney, Agent, or Firm*—Bacon & Thomas, PLLC

(57) ABSTRACT

A skin care device includes a suction nozzle for drawing and removing sebum or other impurities from a user's skin while contacting the skin, a suction pump for generating a suction force for the suction nozzle, a mist nozzle, provided at a position around the suction nozzle, for spraying liquid, a liquid storage tank for storing the liquid to be supplied to the mist nozzle, a liquid supply pump for supplying the liquid in the liquid storage tank to the mist nozzle, and a drive motor for operating the suction pump and the liquid supply pump at the same time. Further, the suction pump and the liquid supply pump are disposed opposite to each other.

14 Claims, 16 Drawing Sheets

FOREIGN PATENT DOCUMENTS

| | | | |
|---|---|---|---|
| JP | 53004648 | | 1/1978 |
| JP | 53-135768 | * | 11/1978 |
| JP | 53-149441 | * | 12/1978 |
| JP | S62-188571 | | 12/1987 |
| JP | 08-232847 | | 9/1996 |
| JP | 09-242666 | | 9/1997 |
| JP | 2000-334009 A | * | 12/2000 |
| JP | 2001-161438 | | 6/2001 |
| JP | 2001-161438 A | * | 6/2001 |
| JP | 2005-342135 A | * | 12/2005 |

* cited by examiner

SKIN CARE DEVICE FOR TAKING OUT AND REMOVING SEBUM OR OTHER CUTANEOUS IMPURITIES

FIELD OF THE INVENTION

The present invention relates to skin care devices; and more particularly, to a skin care device for taking out and removing sebum or other cutaneous impurities from user's skin with a suction nozzle placed against the skin, while the contacting between the suction nozzle tip and the skin is improved by spraying liquid onto the skin around the suction nozzle tip, thereby enhancing the skin care effect.

BACKGROUND OF THE INVENTION

A conventional skin care device treats user's skin with a suction nozzle, which is placed against the skin so that the tip of the suction nozzle touches and covers the skin being treated. When a suction pump of the skin care device is then operated, the tip of the suction nozzle takes out and removes sebum or other cutaneous impurities from the skin (hereinafter, referred to as "skin impurities") while massaging the skin. But since the skin care treatment can be performed while the suction nozzle tip is contacting the skin, a gap may be formed between them. For this reason, the contact made between the suction nozzle of the conventional skin care device and the skin tends to be poor, so that skin impurities cannot be removed sufficiently.

Japanese Patent Laid-open Publication No. 2001-161438 discloses a skin care device which sprays liquid onto the user's skin around the tip of a suction nozzle before and after a sebum suction treatment. Liquid sprayed before the sebum suction treatment helps the tip of the suction nozzle of the skin care device to slide smoothly on the skin, thereby allowing the skin care device easier to maneuver. Further, liquid sprayed after sebum suction treatment helps the irritated skin to be soothed and the skin pores to be closed.

In the skin care device disclosed in Japanese Patent Laid-open Publication No. 2001-161438, a single pump is used as a suction pump and a liquid supply pump. The single pump is provided with both a suction part and an exhaust part so that the single pump draws air into its inner space through a suction port and discharges air to the atmosphere through an exhaust port. To treat the user's skin by taking out and removing skin impurities, the suction nozzle tip is placed against the skin and the pump is operated to draw air from the inner space of the suction part and to discharge the air to the atmosphere through the exhaust part. Thus, the pressure in the suction part is reduced to expel sebum or cutaneous impurities from the skin, thereby cleansing the skin. While this treatment is underway, the tip of the suction nozzle is touching the skin, and a negative pressure is generated inside the suction part so that the exhaust part does not discharge any more air to the atmosphere. Thus, the conventional skin care device, which is configured such that the liquid spraying operation is performed by using the Venturi effect created by the air discharged through the exhaust part, cannot spray liquid onto the skin during the sebum suction treatment. Consequently, the conventional skin care device cannot supply a proper or uniform amount of liquid to the skin during the sebum suction treatment, so that the conventional skin care device cannot evenly or efficiently remove skin impurities.

Further, when a suction pump and a liquid supply pump are separately provided in the housing of a skin care device and are operated simultaneously to solve the above problem, it then becomes necessary to have the suction pump, a drive unit for the suction pump, the liquid supply pump, a drive unit for the liquid supply pump, a liquid storage tank, and a battery as a power source for the device at proper positions in the housing of the skin care device. However, providing the additional components in the housing increases the weight and size of the skin care device. Furthermore, the above added components would disrupt the weight balance of the skin care device, so that maneuvering the skin care device would become more difficult.

SUMMARY OF THE INVENTION

It is, therefore, an object of the present invention to provide a skin care device capable of supplying liquid to a contact area between the suction nozzle tip and the skin during a process of removing skin impurities by means of the suction nozzle, thus improving the contacting between the suction nozzle tip and the skin and evenly removing the skin impurities without increasing the weight or size of the skin care device.

In accordance with an embodiment of the present invention, there is provided a skin care device including: a suction nozzle to draw and remove skin impurities from a user's skin while being in contact with the skin; a suction pump to generate a suction force for the suction nozzle; a mist nozzle provided at a position around the suction nozzle to spray liquid; a liquid storage tank to store the liquid to be supplied to the mist nozzle; a liquid supply pump to supply the liquid in the liquid storage tank to the mist nozzle; and a drive motor to operate the suction pump and the liquid supply pump at the same time.

BRIEF DESCRIPTION OF THE DRAWINGS

The above and other objects and features of the present invention will become apparent from the following description of preferred embodiments given in conjunction with the accompanying drawings, in which:

FIG. 10A illustrates the ON-state of the switch in which the switch is turned on to spray liquid, and FIG. 10B the OFF-state of the switch in which the switch is turned off to stop the ejecting of liquid;

DETAILED DESCRIPTION OF THE PREFERRED EMBODIMENTS

Figure 1:
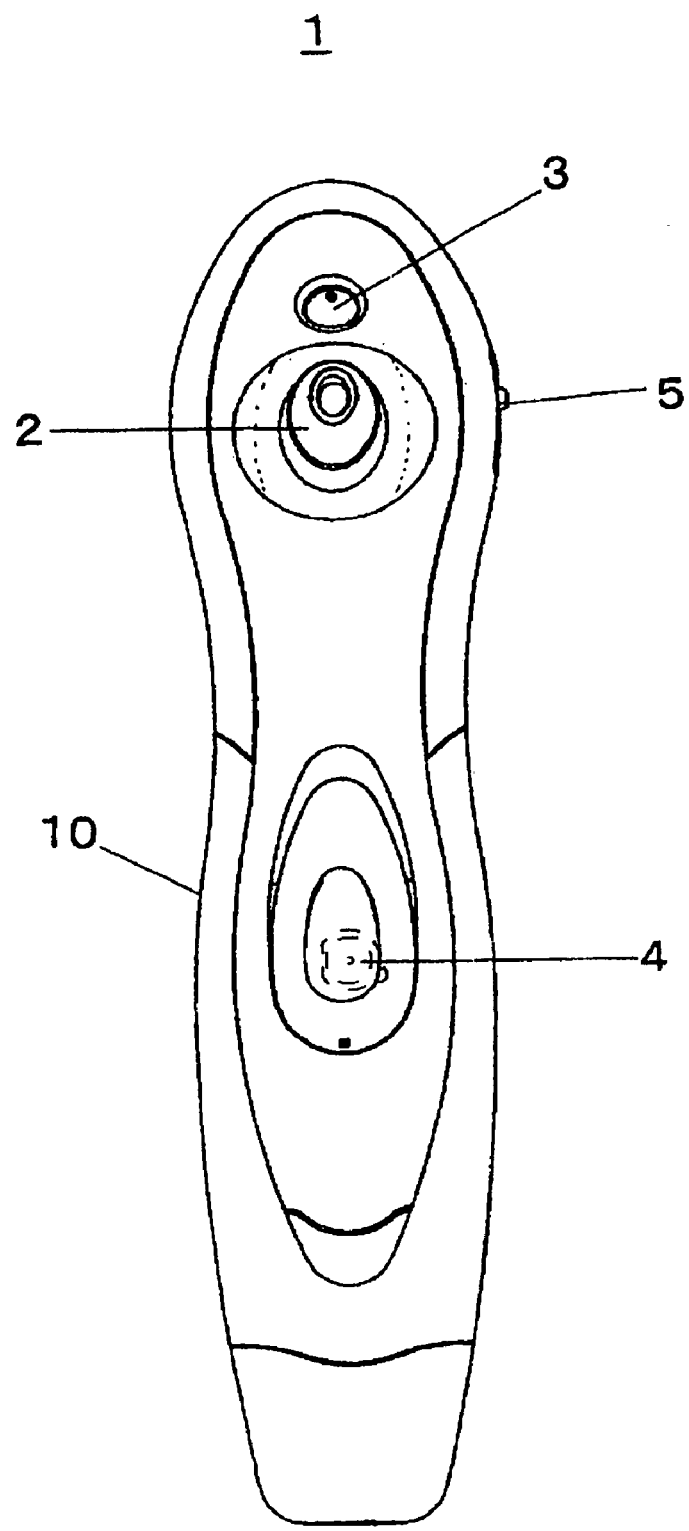
FIG. 1 is a front view illustrating the appearance of a skin care device in accordance with a first embodiment of the present invention.
Figure 2:
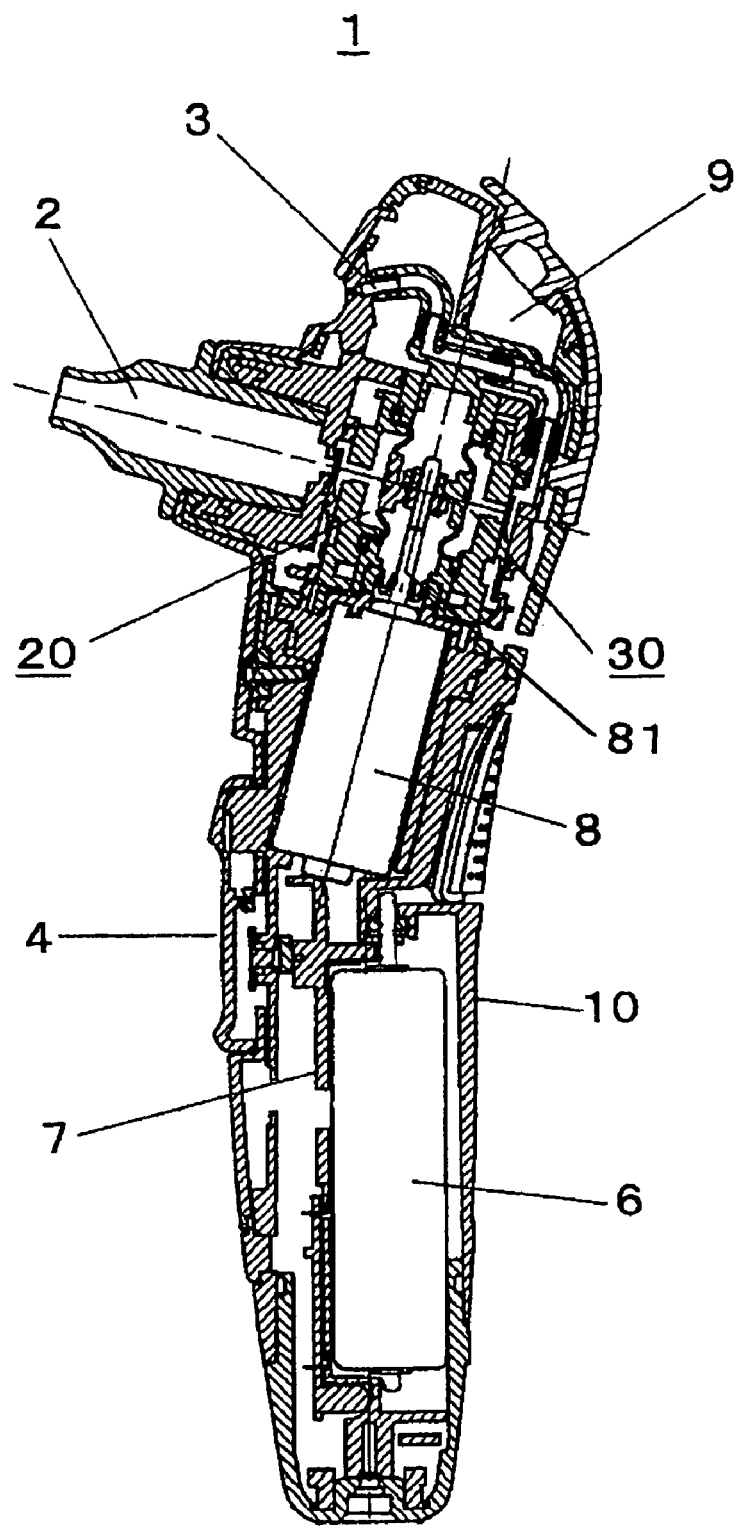
FIG. 2 is a side sectional view illustrating the internal construction of the skin care device shown in FIG. 1.

The first embodiment of the present invention will now be described in detail with reference to the accompanying drawings. FIG. 1 is a front view illustrating the appearance of a skin care device 1 in accordance with the embodiment of the present invention. FIG. 2 is a side sectional view illustrating the internal construction of the skin care device shown in FIG. 1.

As shown in FIG. 1, the skin care device 1 includes a housing 10, with a grip formed by a lower part of the housing 10 to allow a user to hold the device 1. A suction nozzle 2 is provided around the central portion of an upper part of the housing 10. Provided at a predetermined position above the suction nozzle 2 is a mist nozzle 3 to spray liquid onto the user's skin. The housing 10 further includes a main switch 4 and a mist control switch 5. The main switch 4 is provided on an approximately central portion of a front surface of the housing 10, and is operated to turn on or off the skin care device 1, thereby controlling the skin impurities suction operation of the device 1. The mist control switch 5 is provided at an upper position of a side surface of the housing 10 to control the liquid ejecting operation of the device 1.

As shown in FIG. 2, a battery 6, which is, for example, a rechargeable secondary battery to supply electricity to the skin care device 1, and a contact terminal 7 of the main switch 4 are installed in the grip portion of the housing 10. Furthermore, a drive motor 8 is provided along an approximately longitudinal central portion of the housing 10. Both a suction pump 20 and a liquid supply pump 30 are disposed in the housing 10 at positions above the drive motor 8 and in back of the suction nozzle 2 such that the two pumps 20 and 30 are opposite to each other, with a rotating shaft 81 of the drive motor 8 interposed between the two pumps 20 and 30. A liquid storage tank 9 to store therein liquid, such as water, is disposed in the housing 10 above the liquid supply pump 30. The suction nozzle 2 is formed as an attachment so that it can be detached from the suction pump 20.

In the skin care device 1 according to the first embodiment of the invention, both the suction pump 20 and the liquid supply pump 30 are operated by a single motor which is the drive motor 8, so that the two pumps 20 and 30 can be operated at the same time. Thus, the suction operation for drawing and removing the skin impurities using the suction nozzle 2 and the liquid spraying operation for spraying the liquid onto the skin using the mist nozzle 3 can be performed at the same time. The above-mentioned structure with the two pumps 20 and 30 operated by the single drive motor 8 provides further advantages in that the size of the housing 10 can be reduced, and the skin care device 1 has a desirable weight balance and is convenient to use.

Figure 3:
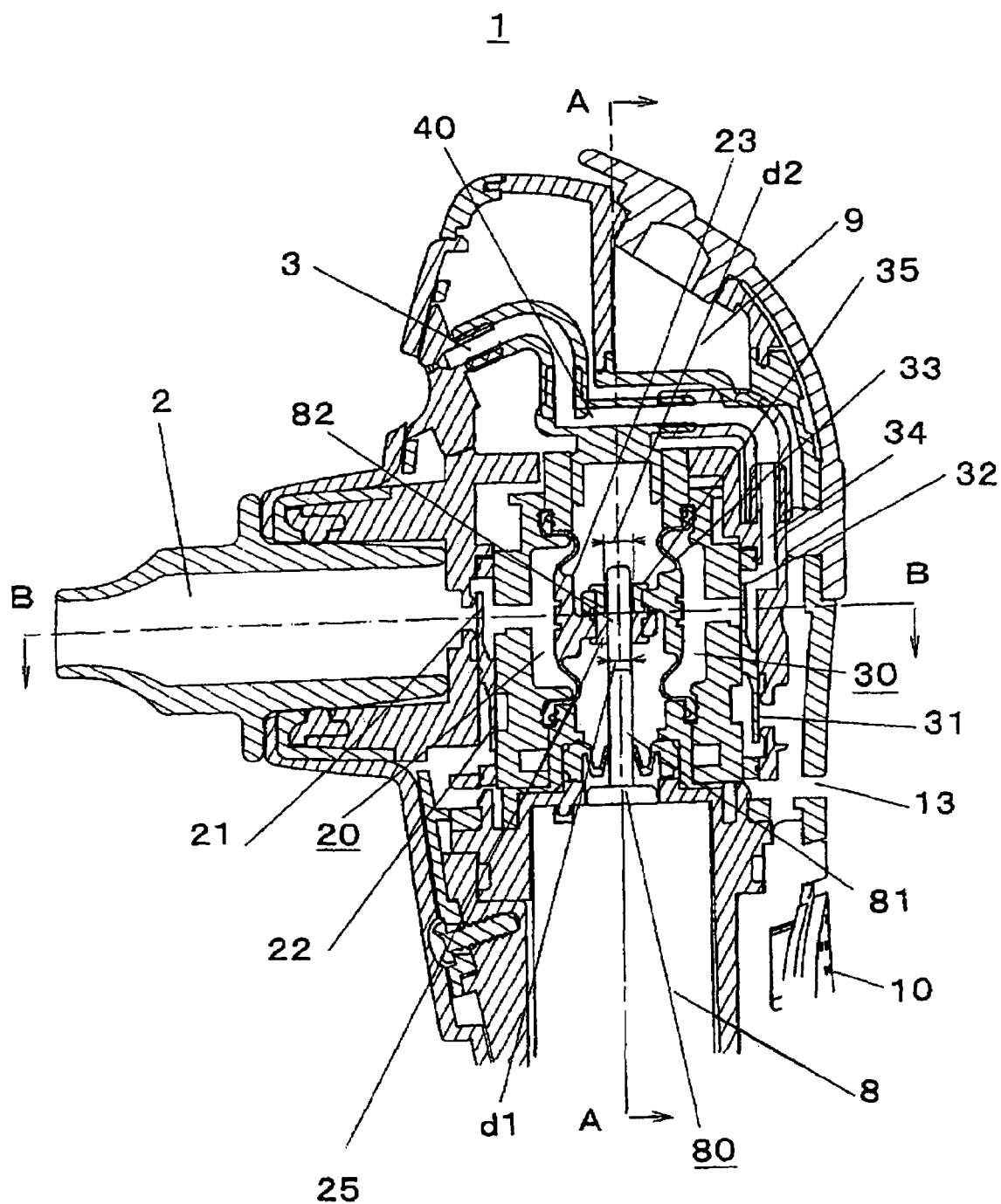
FIG. 3 is an enlarged sectional view illustrating the construction of a section above a drive motor of the skin care device shown in FIG. 2.

FIG. 3 is an enlarged sectional view illustrating the construction of a part above the drive motor 8 of the skin care device 1 shown in FIG. 2. As shown in FIG. 3, the suction pump 20 includes a suction valve 21 and an exhaust valve 22. The suction valve 21 opens or closes the rear end of the suction nozzle 2. The exhaust valve 22 is integrated with the suction valve 21, and executes its ON/OFF operation opposite to the ON/OFF operation of the suction valve 21. The suction pump 20 further includes an elastic body 23 which can be deformed to change the inner volume of the suction pump 20. The elastic body 23 is configured as a diaphragm in the embodiment.

When the elastic body 23 is deformed in the direction that increases the inner volume of the suction pump 20, the suction valve 21 is opened, while the exhaust valve 22 is closed. Thus, atmospheric air is drawn into the inner space of the suction pump 20 through the tip of the suction nozzle 2. On the contrary, when the elastic body 23 is deformed in the opposite direction and reduces the inner volume of the suction pump 20, the suction valve 21 is closed, while the exhaust valve 22 is opened. Thus, air is discharged from the inner space of the suction pump 20 to the atmosphere through an exhaust port.

When the elastic body 23 is deformed in the direction that increases the inner volume of the suction pump 20 while the tip of the suction nozzle 2 is contacting the user's skin, the suction valve 21 is opened, while the exhaust valve 22 is closed. Thus, the inner space of the suction nozzle 2 communicates with the inner space of the suction pump 20, resulting in an increase in the inner volume of the suction pump 20 as well as a reduction in the inner pressure of both the suction nozzle 2 and the suction pump 20. On the contrary, when the elastic body 23 is deformed in the opposite direction and reduces the inner volume of the suction pump 20 while the tip of the suction nozzle 2 is contacting the user's skin, the suction valve 21 is closed so that the inner space of the suction nozzle 2 is closed. Thus, the inner pressure of the suction nozzle 2 is maintained constant. When the exhaust valve 22 is then opened, air is discharged from the inner space of the suction pump 20 to the atmosphere through the exhaust port, so that the inner pressure of the suction pump 20 is made equal to the atmospheric pressure. When the above-mentioned alternate deformation of the elastic body 23 is repeated, the pressure in the suction nozzle 2 is gradually reduced to generate a suction force. The suction nozzle 2 thus draws and removes the skin impurities.

Similarly, the liquid supply pump 30 includes a suction valve 31 and an exhaust valve 32. The suction valve 21 is selectively opened to draw atmospheric air into the liquid supply pump 30. The exhaust valve 32 is integrated with the suction valve 31, and executes its ON/OFF operation opposite to the ON/OFF operation of the suction valve 31. The liquid supply pump 30 further includes an elastic body 33 which can be deformed to change the inner volume of the liquid supply pump 30. The elastic body 33 is formed as a diaphragm in the embodiment. In the liquid supply pump 30, an exhaust port 34 is coupled to the inlet of the mist nozzle 3 through a connection pipe 40, so that the air drawn into the liquid supply pump 30 through the suction valve 31 is supplied to the mist nozzle 3 through the exhaust port 34 and the connection pipe 40.

Figure 4:
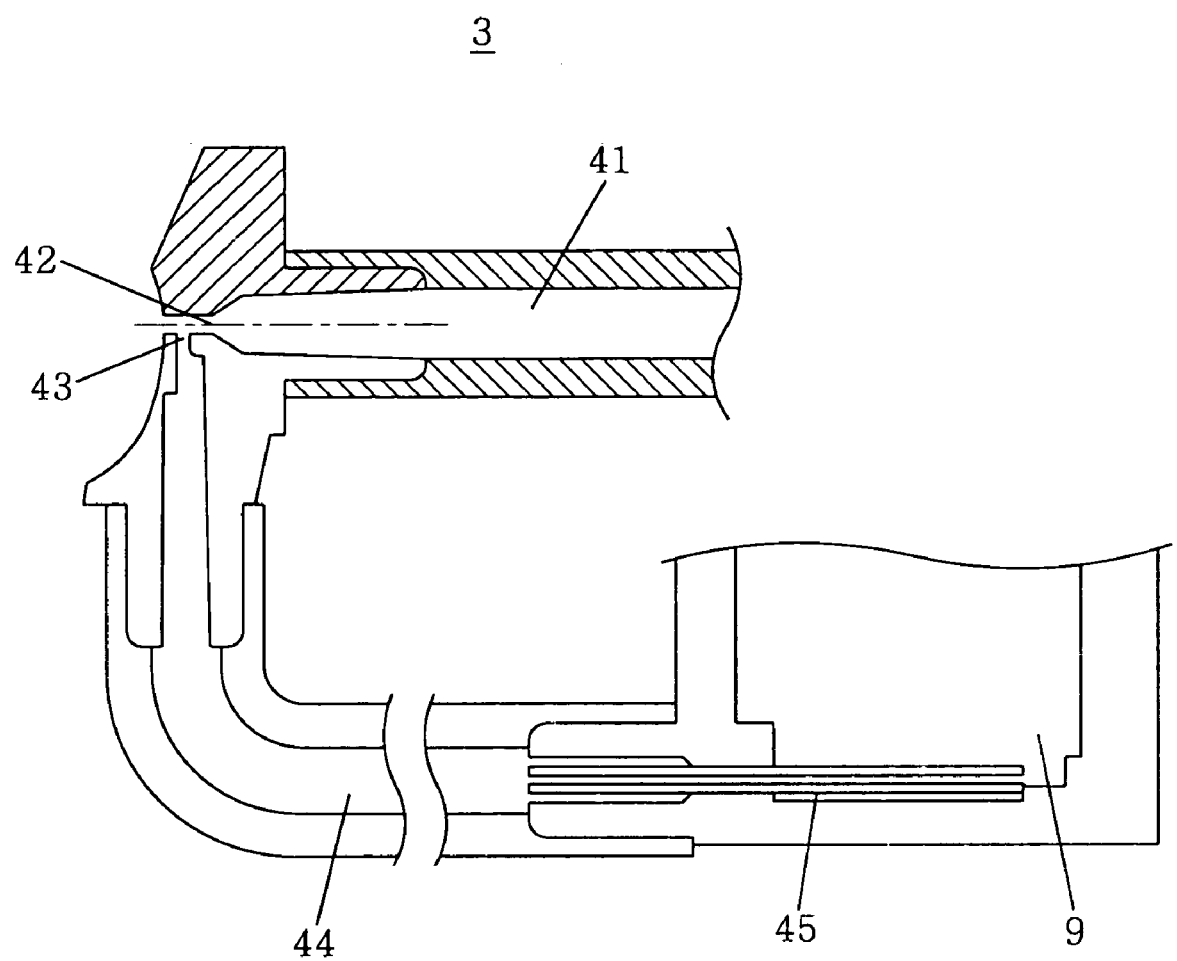
FIG. 4 is a schematic view illustrating the construction of a liquid spray unit provided in the skin care device shown in FIG. 3.

The construction of the mist nozzle 3 is illustrated in FIG. 4. In the mist nozzle 3, air supplied from the liquid supply pump 30 flows through an air pipe 41 and is discharged out at high speed through an air outlet port 42 having a small diameter, so that negative pressure is generated in the air outlet port 42 due to the Venturi effect. Thus, liquid, such as water, is drawn under negative pressure upwards to a liquid outlet port 43 joined with the air outlet port 42, and is sprayed onto the skin around the tip of the suction nozzle 2. The liquid outlet port 43 is connected to the liquid storage tank 9 through a liquid pipe 44. In the mist nozzle 3, a flow rate regulation unit, such as a flow rate regulation pipe 45, is preferably provided in the liquid pipe 44 to regulate the flow rate of the liquid to be sprayed.

Figure 5:
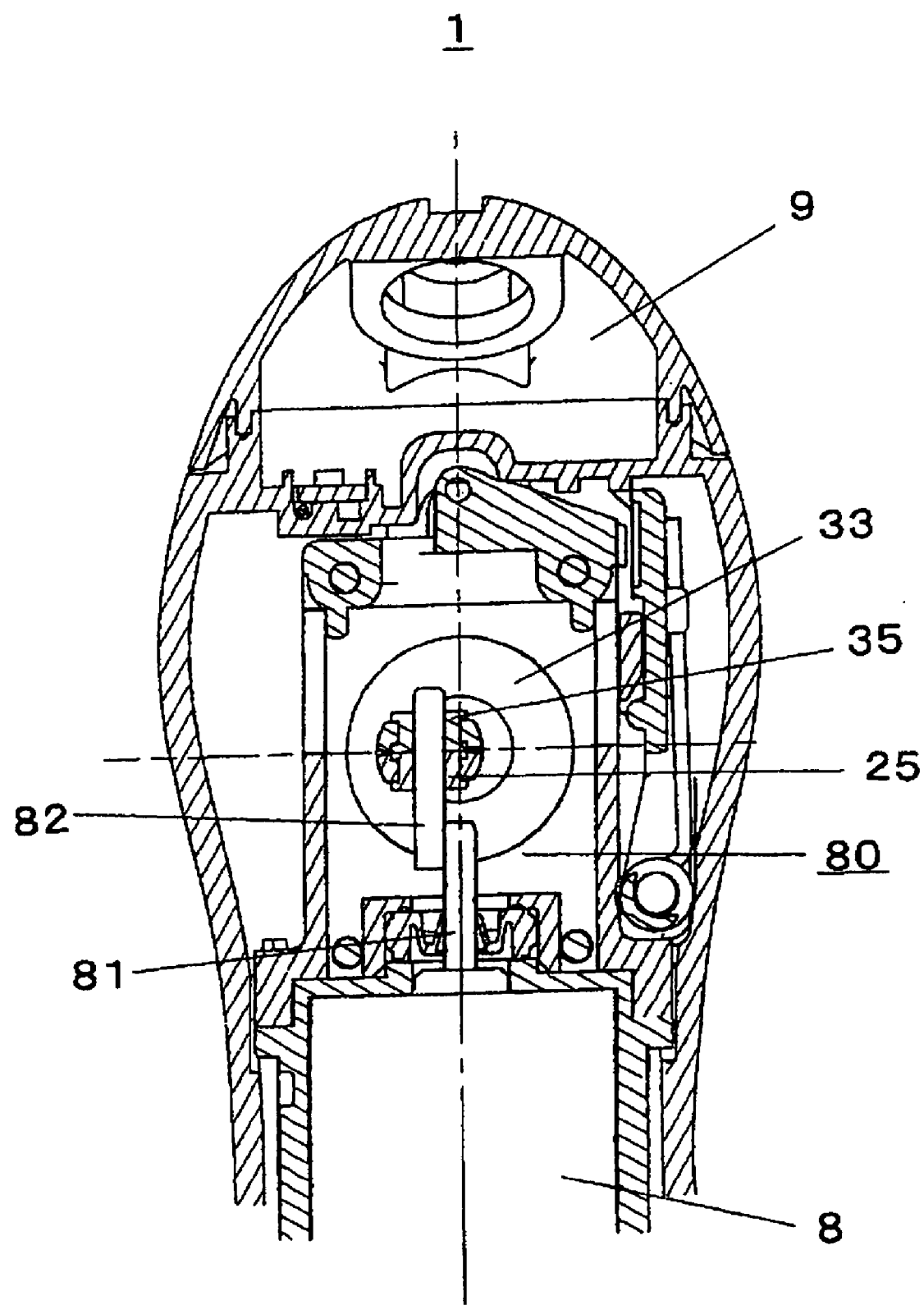
FIG. 5 is a sectional view taken along the line A-A of FIG. 3.
Figure 6:
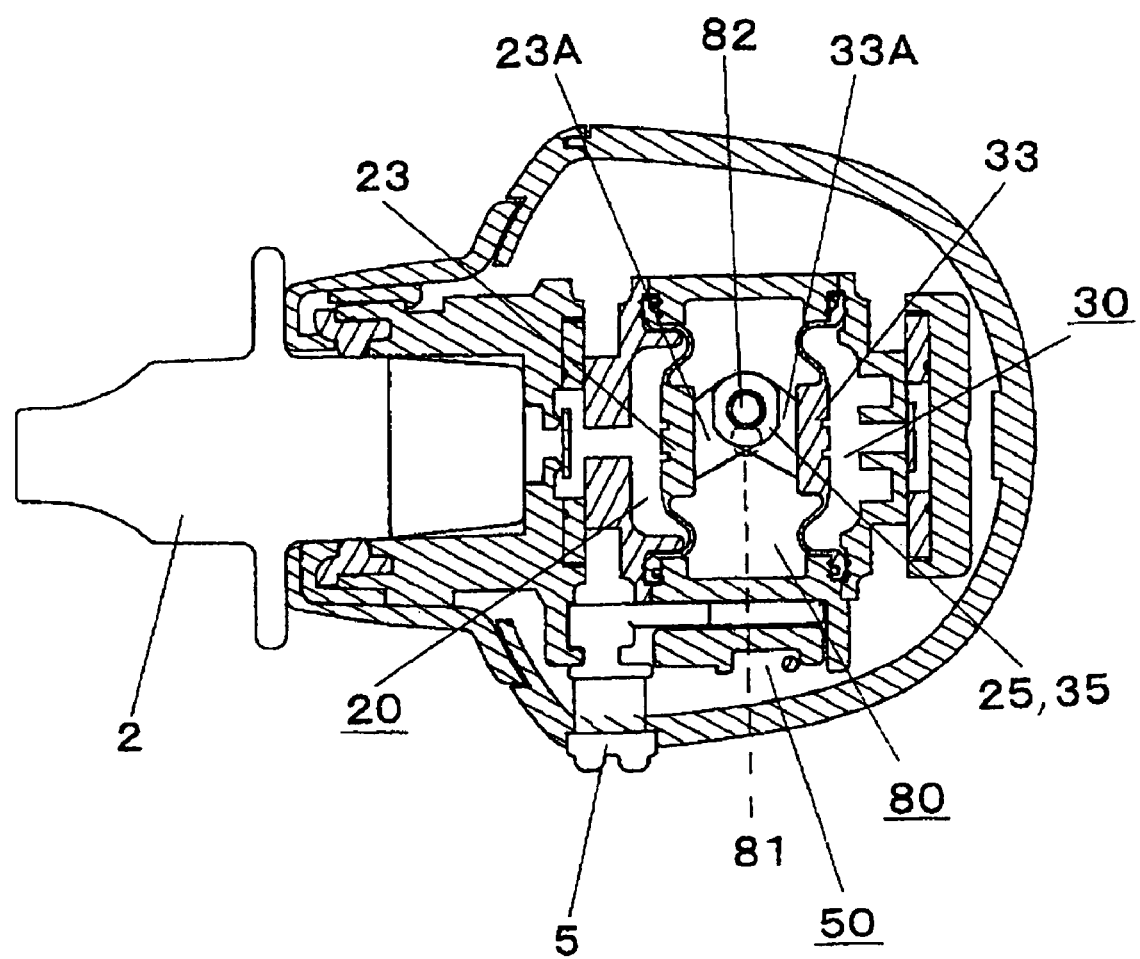
FIG. 6 is a sectional view taken along the line B-B of FIG. 3.

To convert the rotating motion of the rotating shaft 81 of the drive motor 8 into a reciprocating motion in the direction perpendicular to the central axis of the rotating shaft 81, the skin care device 1 includes a motion conversion unit 80 as shown in FIGS. 5 and 6. FIGS. 5 and 6 show sectional views taken along the line A-A and the line B-B of FIG. 3 respectively. As shown in the drawings, the motion conversion unit 80 includes an eccentric member 82 which has a rod shape with a circular cross-section and is axially mounted to the rotating shaft 81 of the drive motor 8 such that the eccentric member 82 is eccentric from the central axis of the rotating shaft 81. The elastic bodies 23 and 33 of both the suction pump 20 and the liquid supply pump 30 are made of an elastic material, for example, rubber, and have protruding connectors 23A and 33A respectively. Each of the protruding connectors 23A and 33A extend toward the rotating shaft 81 of the drive motor 8. Furthermore, the protruding connectors 23A and 33A are respectively provided at their end with bearings 25 and 35 each of which is fitted into the eccentric member 82.

When the rotating shaft 81 of the drive motor 8 rotates, the eccentric member 82 revolves around the rotating shaft 81 with a radius of revolution equal to the eccentricity of the eccentric member 82 from the central axis of the rotating shaft 81. During the revolution of the eccentric member 82 around the rotating shaft 81, the bearings 25 and 35 fitted over the eccentric member 82 revolve around the rotating shaft 81 while sliding on the eccentric member 82 without rotating. Due to the revolution of the bearings 25 and 35 around the rotating shaft 81 of the drive motor 8, the protruding connectors 23A and 33A of the elastic bodies 23 and 33 of both the suction pump 20 and the liquid supply pump 30 reciprocate in directions perpendicular to the central axis of the rotating shaft 81 of the drive motor 8. The elastic bodies 23 and 33 of both the suction pump 20 and the liquid supply pump 30, respectively, are deformable at the central portions thereof and are fixed at the outside edges thereof. Thus, in response to the reciprocating motions of the protruding connectors 23A and 33A, the elastic bodies 23 and 33 are deformed to reduce or increase the inner volumes of both the suction pump 20 and the liquid supply pump 30, respectively.

Furthermore, the deformable portions of the elastic bodies 23 and 33 of both the suction pump 20 and the liquid supply pump 30 are preferably configured to be perpendicular to the reciprocating directions of the protruding connectors 23A and 33A. In addition, the deformable parts of the elastic bodies 23 and 33 are preferably arranged to be opposite and parallel to each other, so that the elastic bodies 23 and 33 can be deformed without interfering with each other. The opposite parallel arrangement of the deformable parts of the elastic bodies 23 and 33 also reduces the size of the housing 10.

In the skin care device 1 of the present invention, both the suction pump 20 and the liquid supply pump 30 are rotated at the same time by the single rotating shaft 81 of the drive motor 8 as described above. Therefore, the liquid may be sprayed onto the user's skin around the tip of the suction nozzle 2 using a negative pressure generated by the discharge of compressed air from the liquid supply pump 30 during a sebum suction operation in which the suction nozzle 2 draws skin impurities using the suction force generated by the suction pump 20. Thus, the skin care device 1 improves sealed contacting necessary between the tip of the suction nozzle 2 with the skin. Furthermore, by using a single drive motor 8, the skin care device 1 can be configured without increasing its weight or the size of the housing 10. In addition, as the suction pump 20, the liquid supply pump 30, the drive motor 8 and the liquid storage tank 9 are concentrically placed above the battery 6 in the housing 10, the skin care device 1 has a desirable weight distribution for balance and is convenient to use.

Figure 7:
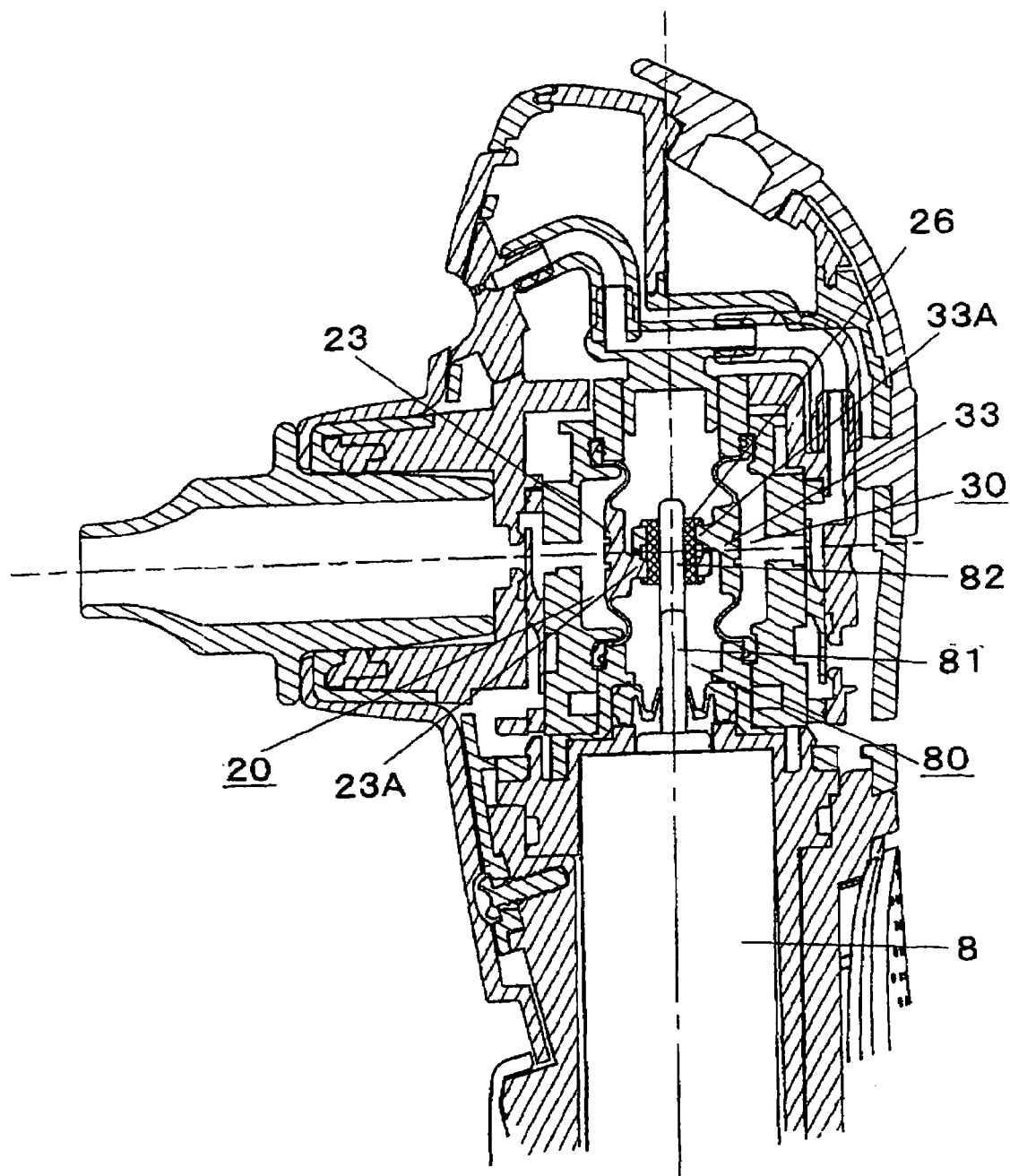
FIG. 7 is a side sectional view illustrating the construction of a part of a skin care device in accordance with a modification of the first embodiment of the present invention.

Hereinafter, a skin care device 1 in accordance the embodiment of the present invention having a modification will be described. In this modification illustrated in FIG. 7, the protruding connectors 23A and 33A of the two elastic bodies 23 and 33 are commonly operated in conjunction with a single bearing 26. The bearing 26 is provided to reduce friction between the eccentric member 82 and the protruding connectors 23A and 33A of the two elastic bodies 23 and 33. Although the single bearing 26 is used with the two protruding connectors 23A and 33A of the elastic bodies 23 and 33 as described above, the skin care device 1 yields the same operational effect as that described above. Furthermore, the use of the single bearing 26 reduces the number of parts of the skin care device 1, resulting in manufacturing costs saving of the device 1. However, in this modification, the protruding connectors 23A and 33A of the elastic bodies 23 and 33 of both the suction pump 20 and the liquid supply pump 30 are not rotated in the same direction relative to the single bearing 26. Thus, friction may be generated between the bearing 26 and the protruding connectors 23A and 33A of the two elastic bodies 23 and 33. Therefore, to reduce the friction generated on all of the junction surfaces between the eccentric member 82 and the protruding connectors 23A and 33A of the two elastic bodies 23 and 33, the skin care device 1 is configured such that two bearings 25 and 35 are respectively provided to the two protruding connectors 23A and 33A of the elastic bodies 23 and 33 as illustrated in FIG. 3, although the two bearings 25 and 35 increase the number of parts of the skin care device 1.

The suction power of the suction pump 20 and the aerodynamic capacity of the liquid supply pump 30 are determined by the strains on (displacements of) the two elastic bodies 23 and 33, respectively. However, in the skin care device 1 of the present invention, both the suction pump 20 and the liquid supply pump 30 use a common drive motor 8 and a common eccentric member 82, so that it is impossible to independently control the suction power of the suction pump 20 and the aerodynamic capacity of the liquid supply pump 30. Furthermore, when the two elastic bodies 23 and 33 are configured to have the same structure so as to reduce the manufacturing costs of the device 1, the suction power of the suction pump 20 and the aerodynamic capacity of the liquid supply pump 30 are equal to each other. Thus, to make the suction power of the suction pump 20 and the aerodynamic capacity of the liquid supply pump 30 different from each other, the two bearings 25 and 35 are configured such that the two bearings 25 and 35 have different inner diameters $d_1$ and $d_2$, as shown in FIG. 3. That is, $d_1 > d_2$, or $d_1 < d_2$. When one of the inner diameters $d_1$ and $d_2$ of the two bearings 25 and 35 is larger than the other, the gap between the bearing 25 or 35 having the larger inner diameter $d_1$ or $d_2$ and the eccentric member 82 increases. Thus, dynamic loss caused during the revolution of the larger inner diameter bearing 25 or 35 around the eccentric member 82 is increased, so that the strain on (displacement of) the elastic body 23 or 33 associated with the larger inner diameter bearing 25 or 35 is reduced. Thus, it is possible to make the suction power of the suction pump 20 and the aerodynamic capacity of the liquid supply pump 30 different from each other although the suction pump 20 and the liquid supply pump 30 use both a common drive motor 8 and a common eccentric member 82, and the two elastic bodies 23 and 33 are configured to have the same structure. Therefore, the skin care device 1 can spray a proper amount of liquid onto the skin according to the suction power of the suction pump 20.

Figure 8:
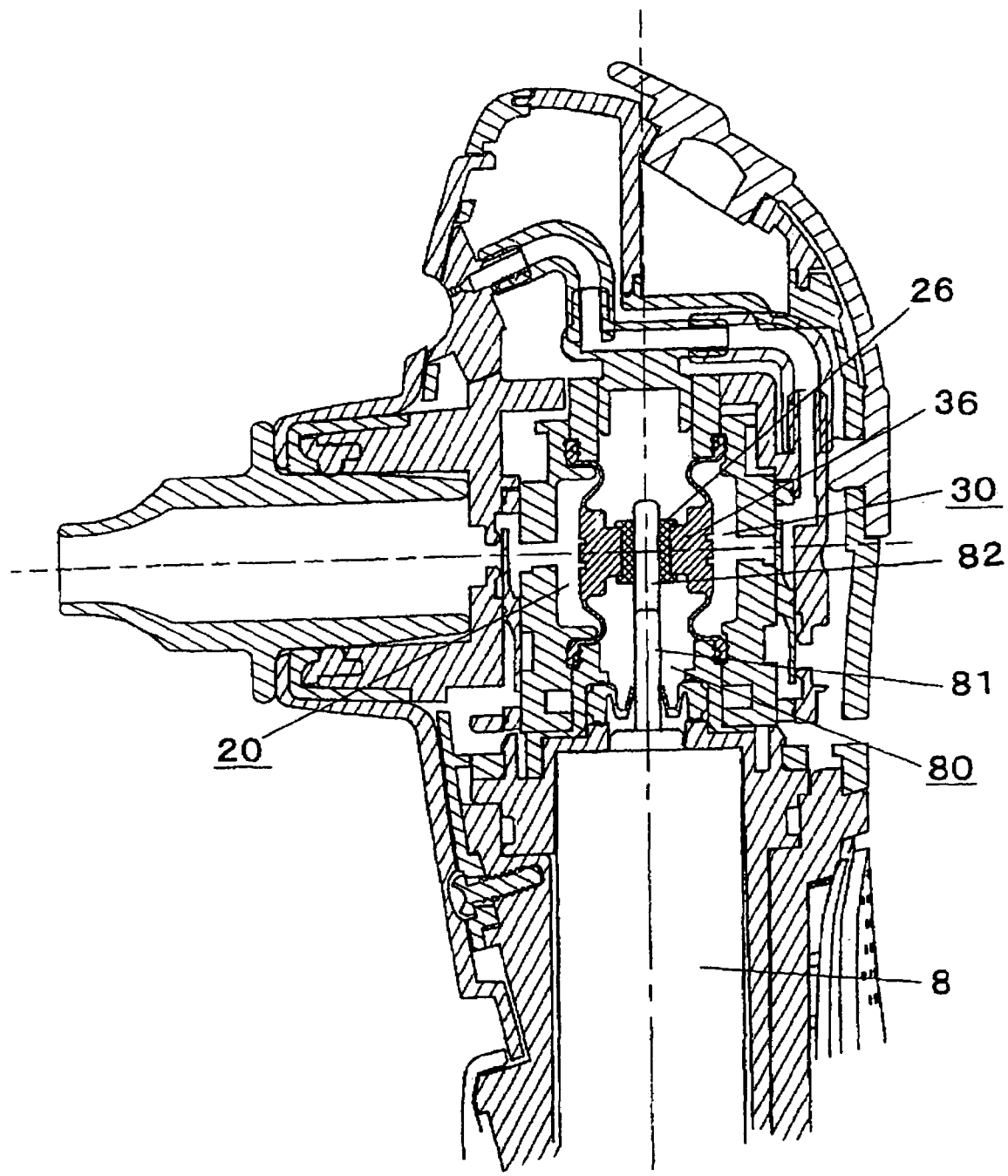
FIG. 8 is a side sectional view illustrating the construction of a part of a skin care device in accordance with another modification of the first embodiment of the present invention.

In case it is necessary that the suction power of the suction pump 20 and the aerodynamic capacity of the liquid supply pump 30 are equal to each other, an integrated single elastic body 36 coupled to a single bearing 26 is preferably used as shown in FIG. 8, in place of the separate elastic bodies 23 and 33 of both the suction pump 20 and the liquid supply pump. This modification reduces the number of parts and satisfies the demands for compact, light and small skin care device 1. Furthermore, the number of slide surfaces between the parts is reduced, thus lowering the operational noise of the device 1.

Figure 9:
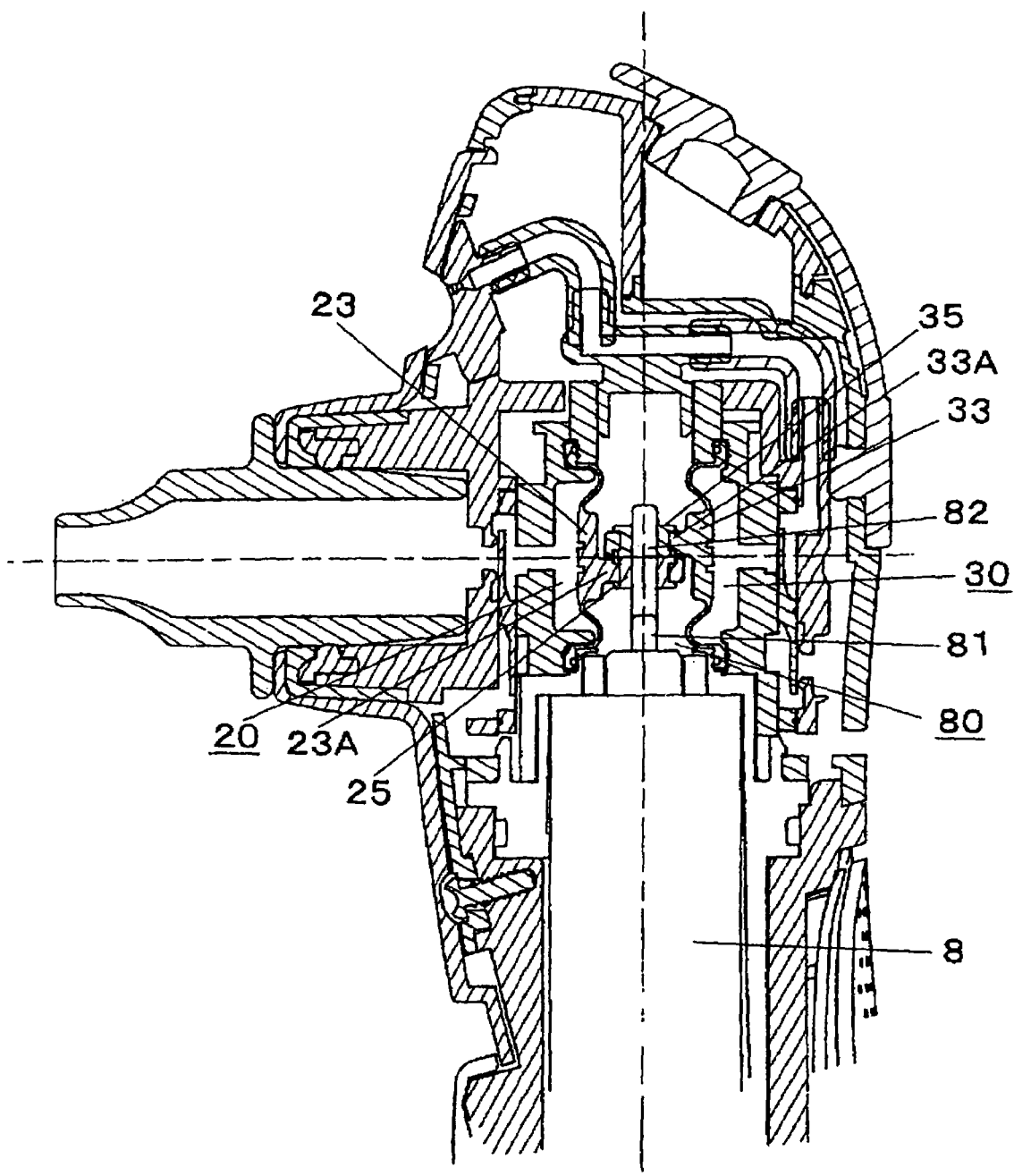
FIG. 9 is a side sectional view illustrating the construction of a part of a skin care device in accordance with a further modification of the first embodiment of the present invention.

In a further modification of the embodiment illustrated in FIG. 9, the upper portion of the drive motor 8 and the lower portions of both the suction pump 20 and the liquid supply pump 30 are changed such that a part of the upper portion of the drive motor 8 is placed between the lower portions of the suction pump 20 and the liquid supply pump 30. This modification reduces the length of the housing 10.

Figure 10A:
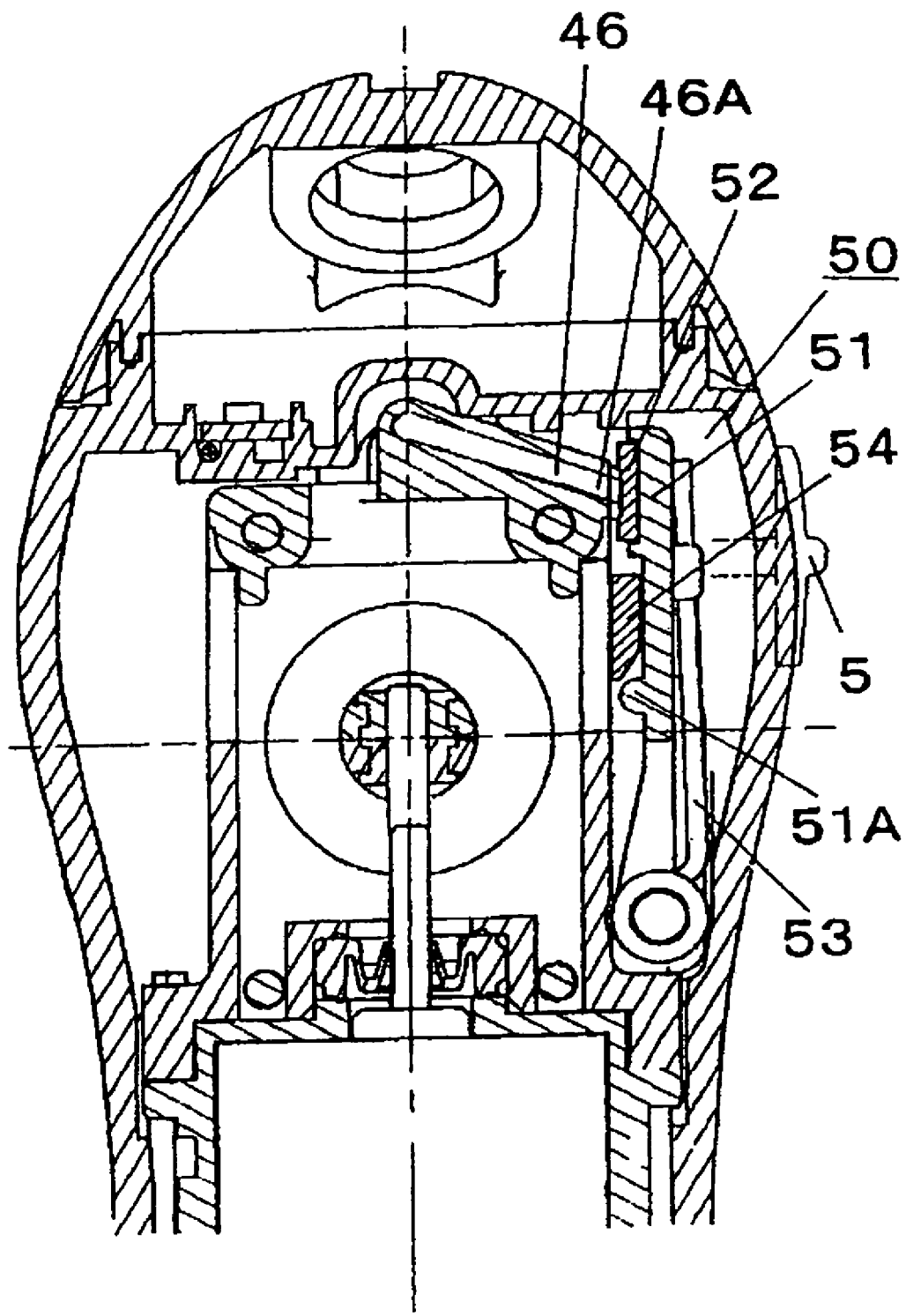
FIGS. 10A and 10B are sectional views illustrating operation of a mist control switch of the skin care device according to the present invention, where
Figure 10B:
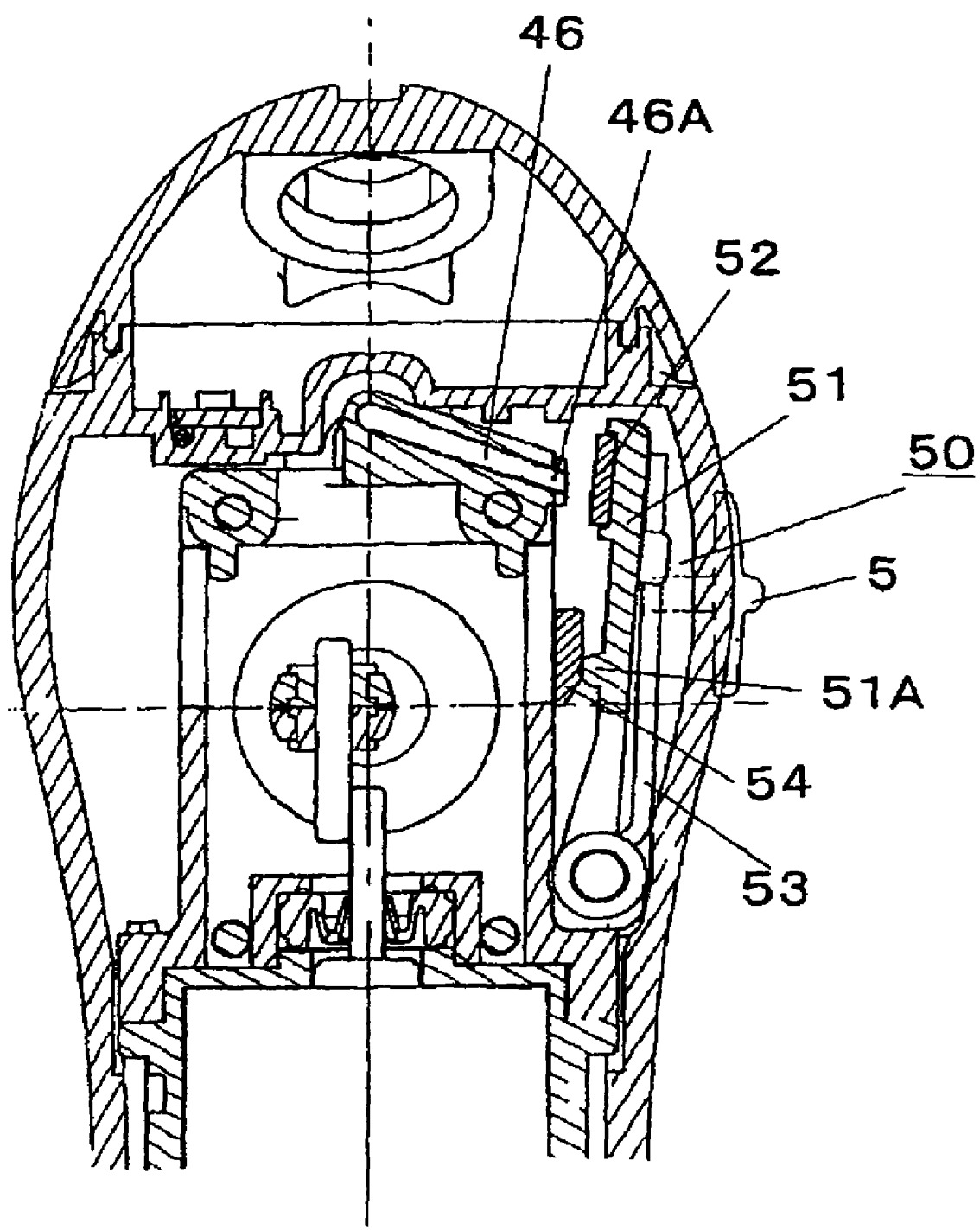

FIGS. 10A and 10B illustrate the operation of the mist control switch 5 of the skin care device 1 in accordance with the present invention. FIG. 10A illustrates the ON-state of the mist control switch 5 in which the switch 5 is turned on to spray liquid. FIG. 10B illustrates the OFF-state of the switch 5 in which the switch 5 is turned off to stop spraying of liquid. As shown in FIGS. 10A and 10B, a branch pipe 46 is provided on the connection pipe extending from the liquid supply pump 30 to the mist nozzle 3 such that the outlet end 46A thereof is open to the atmosphere. A branch pipe control unit 50 is provided at a predetermined position around the liquid supply pump 30 in the housing 10 to open or close the branch pipe 46. In the embodiment of the drawings, the branch pipe control unit 50 is preferably installed at the lower space provided between the suction pump 20 and the liquid supply pump 30 as shown in FIG. 6. The branch pipe control unit 50 includes a rotary lever 51, an ON/OFF pad 52, a spring 53, and a movable control member 54. The rotary lever 51 having an actuating protrusion 51A is rotatably supported by a hinge in the housing 10. The ON/OFF pad 52 is provided at a distal end of the rotary lever 51 to open or close the outlet end 46A of the branch pipe 46. The spring 53 normally biases the rotary lever 51 in a direction which allows the ON/OFF pad 52 to close the outlet end 46A of the branch pipe 46. The movable control member 54 is moved in combination with the operation of the mist control switch 5, and controls the rotating motion of the rotary lever 51 due to its variable position.

When a user turns on the mist control switch 5, the movable control member 54 is moved upwards as viewed from in FIG. 10A. Thus, the rotary lever 51 is rotated counterclockwise by the biasing force of the spring 53, so that the ON/OFF pad 52 closes the outlet end 46A of the branch pipe 46. Therefore, compressed air from the liquid supply pump 30 flows into the mist nozzle 3, so that the mist nozzle 3 sprays the liquid onto the skin of the user. On the contrary, when the user turns off the mist control switch 5, the movable control member 54 is moved downwards as viewed from FIG. 10B, thus pushing the actuating protrusion 51A of the rotary lever 51. Therefore, the rotary lever 51 is rotated clockwise while overcoming the biasing force of the spring 53, so that the ON/OFF pad 52 is separated from the outlet end 46A of the branch pipe 46. As a result, the branch pipe 46 is opened, so that most of the compressed air from the liquid supply pump 30 flows into the branch pipe 46 without being introduced into the mist nozzle 3. The liquid is not sprayed from the mist nozzle 3. Thus, the skin care device 1 selectively sprays or stops spraying the liquid in response to the user's manipulation of the mist control switch 5.

The movable control member 54 is inclined at a contact part thereof at which the member 54 comes into contact with the actuating protrusion 51A of the rotary lever 51. Thus, when the mist control switch 5 is moved to an approximately intermediate position between the ON and OFF positions, it is possible to control the opening ratio of the outlet end 46A of the branch pipe 46 by the ON/OFF pad 52. Then, a part of the compressed air from the liquid supply pump 30 flows into the branch pipe 46, while the remaining part of the compressed air flows into the mist nozzle 3. Thus, the amount of compressed air flowing into the mist nozzle 3 can be controlled, so that it is possible to control the amount of liquid sprayed from the mist nozzle 3 as desired.

Figure 11:
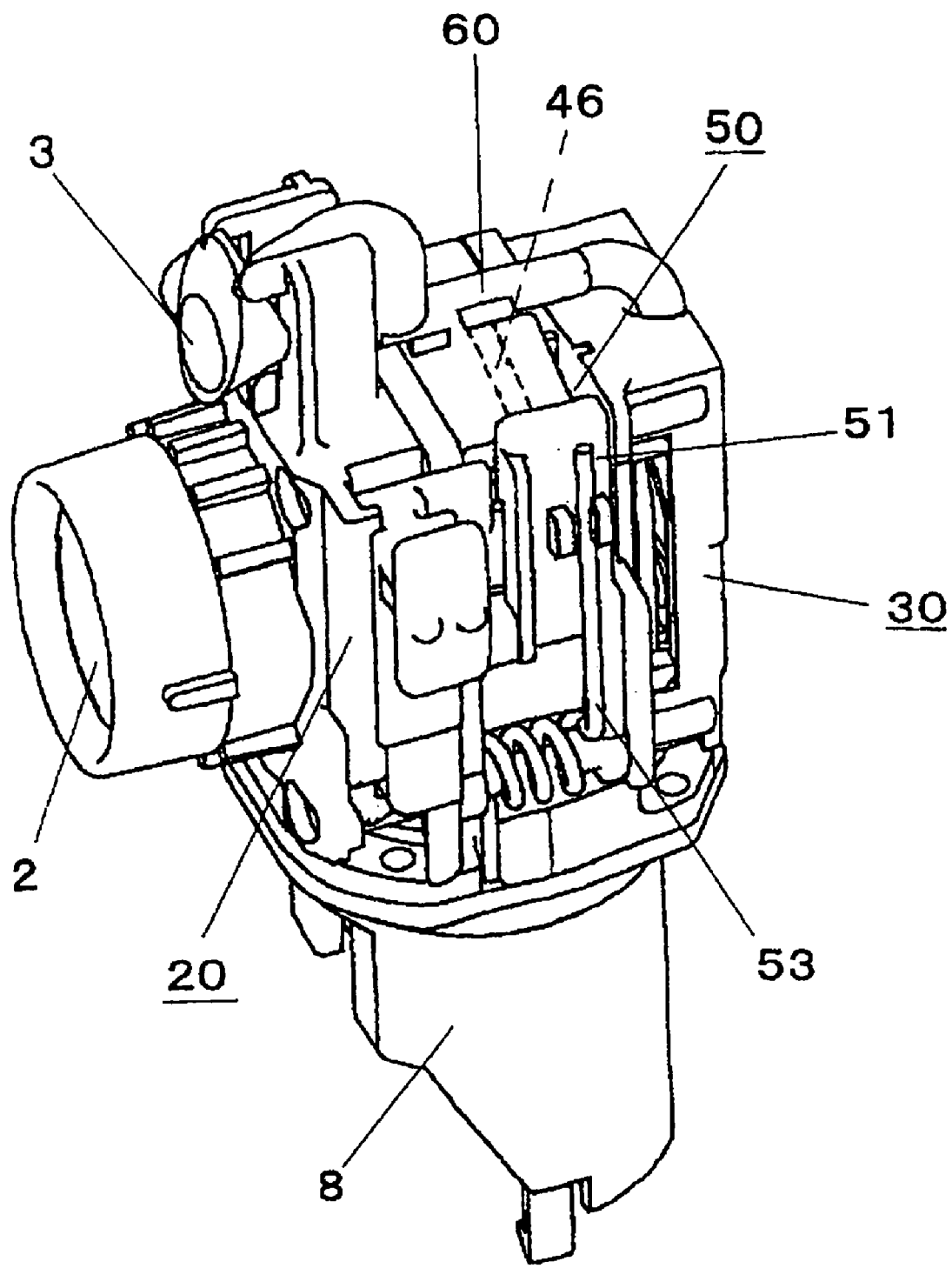
FIG. 11 is a perspective view illustrating a motor/pump unit into which a drive motor, a suction pump and a liquid supply pump of the skin care device of the present invention are integrated.

FIG. 11 is a perspective view illustrating a motor/pump unit into which the drive motor 8, the suction pump 20 and the liquid supply pump 30 are integrated. As shown in FIG. 11, a connection pipe 60 extending between the liquid supply pump 30 and the mist nozzle 3, and the branch pipe 46 are arranged along the outer surface of the motor/pump unit, while the branch pipe control unit 50 is arranged between the suction pump 20 and the liquid supply pump 30. The above-mentioned arrangement of the components reduces the size of a motor/pump unit and shortens the conduit lines to reduce the head loss from the conduit lines.

Figure 12:
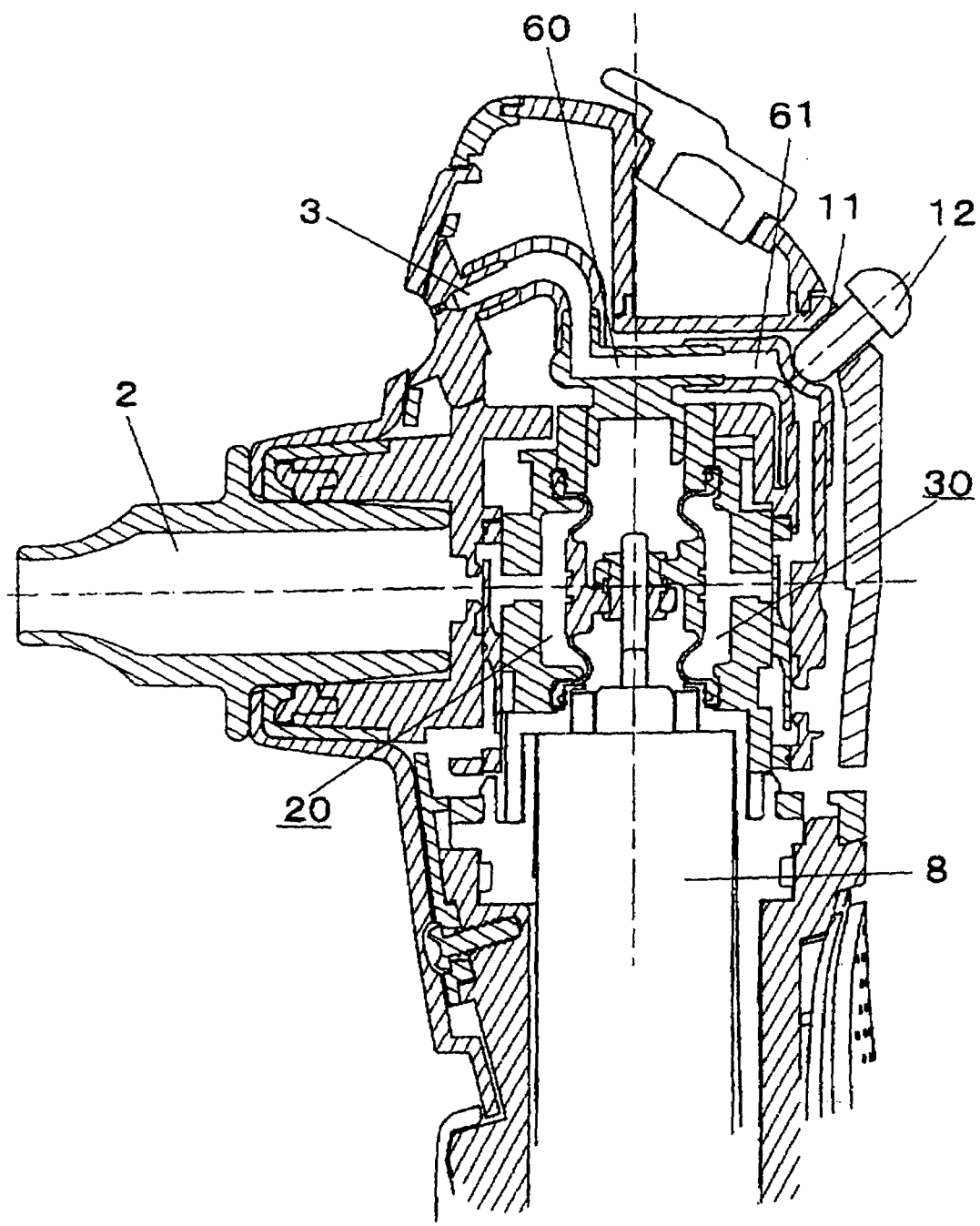
FIG. 12 is a side sectional view illustrating the construction of a part of a skin care device in accordance with yet another modification of the first embodiment of the present invention.

FIG. 12 illustrates a skin care device in accordance with yet another modification of the embodiment of the present invention in which, in place of the mist control switch 5 and the branch pipe control unit 50, a shutoff unit to control the flow of compressed air from the liquid supply pump 30 is provided on the connection pipe 60 extending between the liquid supply pump 30 and the mist nozzle 3. In a detailed description, the shutoff unit includes an opening 11 provided at an upper position on the rear surface of the housing 10. A control button 12 is inserted into the opening 11 so that the button 12 is controlled outside the housing 10. Furthermore, a contact part 61 of the connection pipe 60 which is in contact with the inside end of the control button 12 is made of an elastic material, such as rubber, so that the contact part 61 of the pipe 60 is deformable. Thus, when a user pushes the control button 12 into the housing 10, the control button 12 elastically compresses the deformable contact part 61 of the connection pipe 60 so that the inner diameter of the contact part 61 may be reduced to a desired level or the contact part 61 may be fully contracted until the part 61 is closed. Thus, the flow rate of the compressed air flowing in the connection pipe 60 can be set to a desired level, or reduced to zero. Thus, a user controls the amount of liquid sprayed from the mist nozzle 3 as desired, or stops the ejecting of the liquid.

Figure 13:
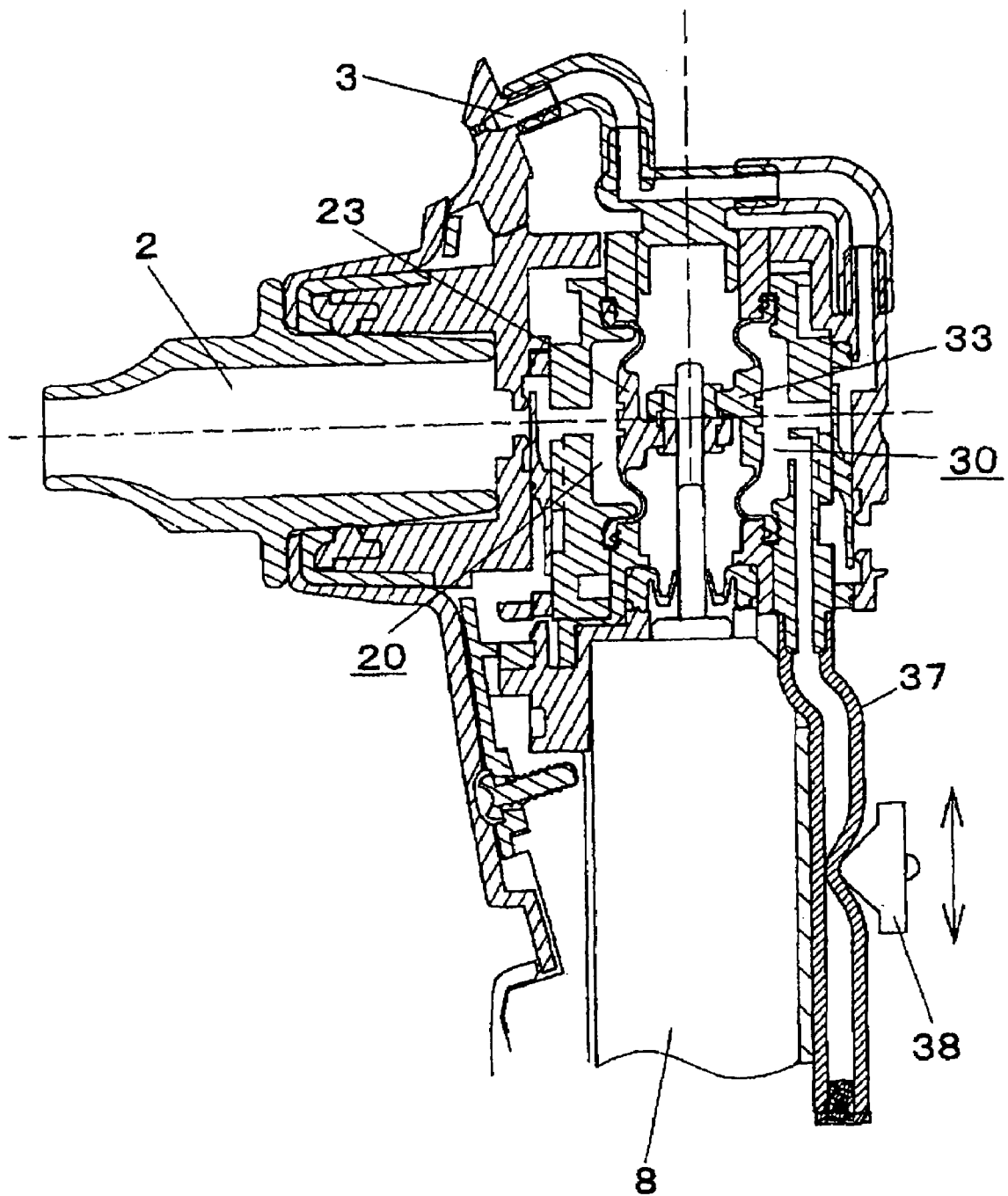
FIG. 13 is a side sectional view illustrating the construction of a part of a skin care device in accordance with still another modification of the first embodiment of the present invention.

FIG. 13 illustrates a skin care device in accordance with still another modification of the embodiment of the present invention in which the pressure of compressed air generated in the liquid supply pump 30 can be controlled as desired. As shown in FIG. 13, a tube 37 made of an elastic material, such as rubber, is connected to the liquid supply pump 30 so that the inner volume of the pump 30 is increased. Furthermore, a pump volume control switch 38 is provided on the rear surface of the housing 10 so that the switch 38 is moved in a vertical direction along the housing 10 while compressing the tube 37 to close the tube 37 at a desired position. Thus, it is possible to vary the inner volume of the liquid supply pump 30 by adjusting the position of the switch 38.

As described above, the flow of compressed air from the liquid supply pump 30 is caused by the strain on or displacement of the elastic body 33. However, when the displacement of the elastic body 33 is constant, the pressure of compressed air from the liquid supply pump 30 varies inversely proportional to the inner volume of the liquid supply pump 30. Thus, when the pump volume control switch 38 is placed at a lower position to increase the inner volume of the liquid supply pump 30, the pressure of compressed air from the liquid supply pump 30 is reduced, resulting in a reduction in the amount of liquid sprayed from the mist nozzle 3. On the contrary, when the pump volume control switch 38 is placed at a higher position to decrease the inner volume of the liquid supply pump 30, the pressure of the compressed air from the liquid supply pump 30 is increased, resulting in an increase in the amount of liquid sprayed from the mist nozzle 3. Thus, it is possible to control the amount of liquid sprayed from the mist nozzle 3 by adjusting the position of the pump volume control switch 38.

Figure 14A:
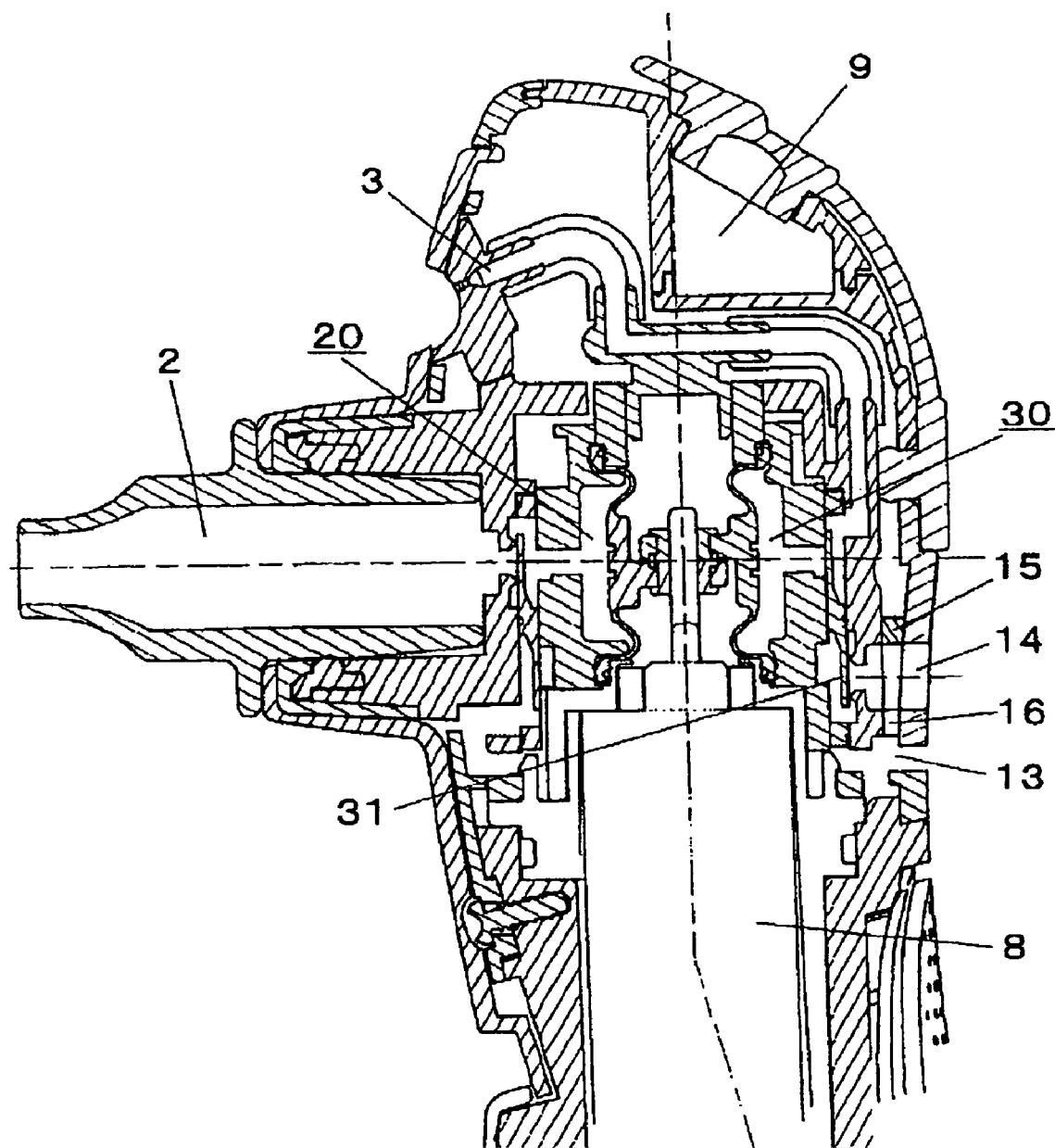
FIGS. 14A and 14B show a side sectional view illustrating the construction of a part of a skin care device in accordance with still another modification of the first embodiment of the present invention, and a view illustrating a part of a housing of the skin care device shown in FIG. 14A, respectively.
Figure 14B:
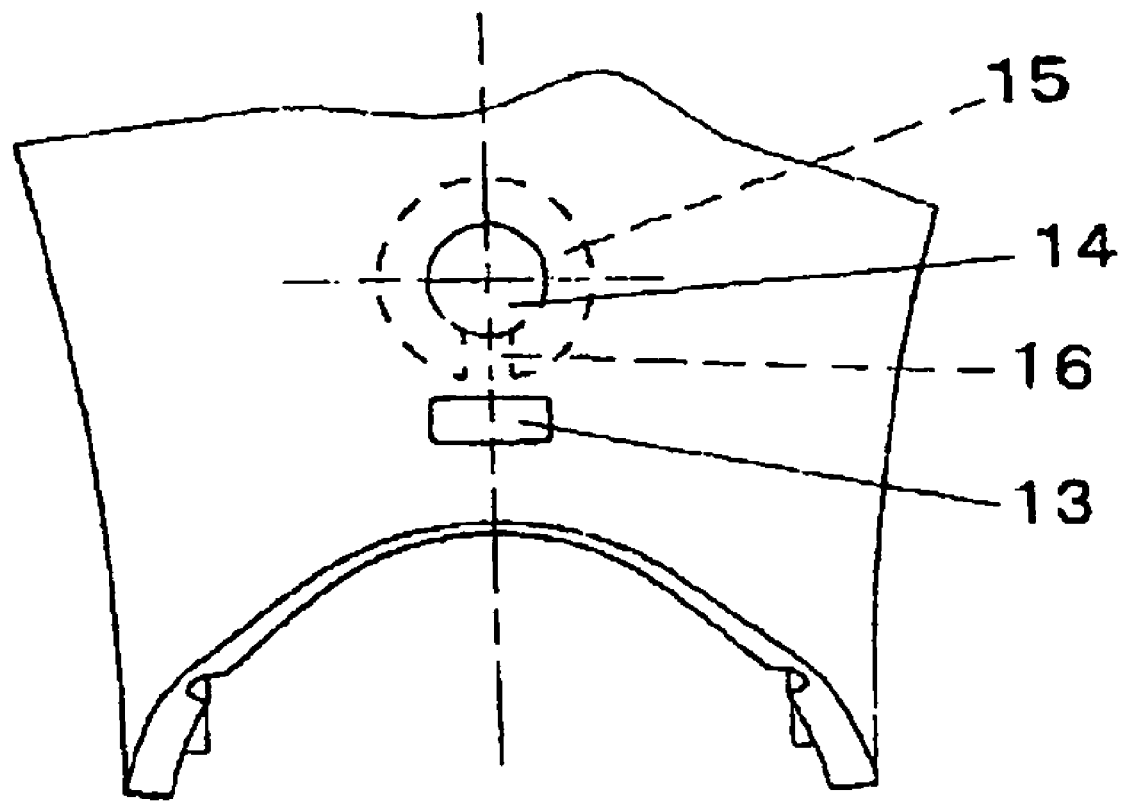

In the skin care device 1 in accordance with the present invention, both the suction pump 20 and the liquid supply pump 30 are operated at the same time by the single drive motor 8, so that liquid sprayed from the mist nozzle 3 may be drawn into the suction nozzle 2. The liquid drawn into the suction nozzle 2 flows into the suction pump 20 and is, thereafter, discharged from the pump 20 through the exhaust port, and is drained from the housing 10 to the outside through a drain hole 13 provided on the rear surface of the housing 10. However, the suction valve 31 of the liquid supply pump 30 is provided at a position just above the drain hole 13 as shown in FIG. 3, so that the drained liquid may be drawn into the suction port of the liquid supply pump 30. When the drained liquid is drawn into the suction port of the liquid supply pump 30, the drained liquid is compressed in the liquid supply pump 30 and discharged along with the compressed air from the mist nozzle 3 at high speed. To avoid the above-mentioned reintroduction of the drained liquid into the liquid supply pump 30, a suction hole 14 is preferably provided on the housing 10 at a position aligned with the suction valve 31 of the liquid supply pump 30 as shown in FIG. 14A. Furthermore, a partition wall 15 is arranged to surround a passage between the suction hole 14 and the suction valve 31 while isolating the suction valve 31 from the other parts as shown in FIGS. 14A and 14B. Because of the above-mentioned structure having the partition wall 15, the suction port of the liquid supply pump 30 directly communicates with the suction hole 14 of the housing 10.

Furthermore, at least one through hole 16 may be formed on a predetermined position of the partition wall 15. Thus, although a user inadvertently closes the suction hole 14 with a finger, the liquid supply pump 30 can draws atmospheric air into its inner space through the through hole 16. However, in that case, liquid drained from the suction pump 20 through the drain hole 13 may be drawn into the liquid supply pump 30 through the suction port of the pump 30. Furthermore, although liquid, such as wash water, flows into the partition wall 15 through the suction hole 14 when the skin care device 1 is washed, the wash water can be easily drained out of the drain hole 13 after passing through the through hole 16.

While the invention has been shown and described with respect to the preferred embodiments, it will be understood by those skilled in the art that various changes and modifications may be made without departing from the spirit and scope of the invention as defined in the following claims.

What is claimed is:

1. A skin care device comprising:
a suction nozzle for drawing and removing skin impurities from a user's skin while contacting the skin;
a suction pump for generating a suction force for the suction nozzle;
a mist nozzle, provided at a position around the suction nozzle, for spraying a liquid;
a liquid storage tank for storing the liquid to be supplied to the mist nozzle;
a liquid supply pump for supplying the liquid in the liquid storage tank to the mist nozzle; and
a drive motor for operating the suction pump and the liquid supply pump at the same time,
wherein the suction pump and the liquid supply pump are disposed opposite to each other with a rotating shaft of the driving motor interposed therebetween.

2. The skin care device of claim 1, wherein each of the suction pump and the liquid supply pump includes an elastic body and a motion conversion unit, provided between the elastic body and the rotating shaft of the drive motor, for converting rotating motion of the rotating shaft of the drive motor into reciprocating motion in a direction perpendicular to a central axis of the rotating shaft.

3. The skin care device of claim 2, wherein the elastic bodies of the suction pump and the liquid supply pump are configured to have different displacements, by connecting the elastic bodies to bearings having a diameter different from each other.

4. The skin care device of claim 2, wherein the drive motor is arranged between the suction pump and the liquid supply pump.

5. The skin care device of claim 2, wherein the elastic bodies of the suction pump and the liquid supply pump are opposite to each other and are formed as a single body.

6. The skin care device of claim 2, further comprising:
a branch pipe, which has an outlet end and is provided on a passage extending from the liquid supply pump to the mist nozzle, the outlet end being opened to an outside; and
a branch pipe control unit, provided at a predetermined position around the liquid supply pump, for opening or closing the branch pipe.

7. The skin care device of claim 2, further comprising:
a shutoff unit, provided on a pipe extending between the liquid supply pump to the mist nozzle, for opening or closing the passage.

8. The skin care device of claim 2, wherein the liquid supply pump has a variable inner volume.

9. The skin care device of claim 2, further comprising:
a suction hole formed at a housing;
a suction port installed at the liquid supply pump; and
a suction hole provided on a housing at a position aligned with the suction valve; and
a partition wall for connecting the suction port with the suction hole.

10. The skin care device of claim 9, wherein the partition wall has at least one through hole.

11. The skin care device of claim 7, wherein the shutoff unit has a control button and the pipe has a deformable contact part in contact with the control button,
wherein a inner diameter of the deformable contact part is reduced by pushing the control button.

12. The skin care device of claim 2, wherein the liquid supply pump has a tube made of an elastic material; and a pump volume control switch compressing the tube, and
wherein an inner volume of the liquid supply pump is varied by adjusting a position of the pump volume control switch.

13. The skin care device of claim 2, wherein the motion conversion unit includes a eccentric member which has a rod shape with a circular cross-section and is axially mounted to the rotating shaft of the drive motor such that the eccentric member is eccentric to a central axis of the rotating shaft.

14. The skin care device of claim 13, wherein each of the elastic bodies has a protruding connector; the protruding connector extends toward the rotating shaft of the drive motor; and the protruding connector is provided at its end with a bearing into which the eccentric member is fitted.

* * * * *